(12) United States Patent
Itoh et al.

(10) Patent No.: US 10,538,679 B2
(45) Date of Patent: Jan. 21, 2020

(54) PHOSPHOR

(71) Applicant: Mitsui Mining & Smelting Co., Ltd., Tokyo (JP)

(72) Inventors: Jun-ichi Itoh, Ageo (JP); Ikuhiro Ozawa, Ageo (JP); Takayoshi Mori, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 289 days.

(21) Appl. No.: 15/533,057

(22) PCT Filed: Feb. 10, 2016

(86) PCT No.: PCT/JP2016/053692
§ 371 (c)(1),
(2) Date: Jun. 5, 2017

(87) PCT Pub. No.: WO2016/140029
PCT Pub. Date: Sep. 9, 2016

(65) Prior Publication Data
US 2017/0335184 A1    Nov. 23, 2017

(30) Foreign Application Priority Data
Mar. 2, 2015  (JP) .................................. 2015-040471

(51) Int. Cl.
| | |
|---|---|
| C09D 7/40 | (2018.01) |
| A61B 5/00 | (2006.01) |
| C09D 1/00 | (2006.01) |
| C09D 5/22 | (2006.01) |
| C09K 11/59 | (2006.01) |

(52) U.S. Cl.
CPC .............. *C09D 7/40* (2018.01); *A61B 5/0066* (2013.01); *A61B 5/0071* (2013.01); *C09D 1/00* (2013.01); *C09D 5/22* (2013.01); *C09K 11/592* (2013.01)

(58) Field of Classification Search
CPC .............. C09K 11/59; C09D 5/22; C09D 7/61
See application file for complete search history.

(56) References Cited

U.S. PATENT DOCUMENTS 5,888,291 A * 3/1999 Chopin .................... A61K 8/25
106/466
2013/0119280 A1  5/2013 Fuchi et al.

FOREIGN PATENT DOCUMENTS

| CN | 103601202 A | 2/2014 |
|---|---|---|
| CN | 104098103 | * 10/2014 |
| CN | 104098103 A | 10/2014 |
| JP | 9-504771 A | 5/1997 |
| JP | 2004-526330 A | 8/2004 |
| JP | 2008-185378 A | 8/2008 |
| JP | 2010-000440 A | 1/2010 |
| WO | 02/091530 A1 | 11/2002 |

OTHER PUBLICATIONS

Abstract for JP 2008-185378, Aug. 14, 2018.*
Abstract for JP 2010-000440, Jan. 7, 2010.*
Sheptyakov et al., "Two types of adjacent dimer layers in a low temperature phase of BaCuSi2o6", Phy. Rev. B, vol. 86, issue 1, Jul. 2012, pp. 014433-1 to 014433-8.*
Translation for CN 104098103, Oct. 15, 2014.*
Chen et al., "Hydrothermal synthesis and propeties of pigments Chinese purple BeCuSi2O6 and dark blue BaCu2Si2O7" < Dyes and Pigments, 105, pp. 167-173, Feb. 2014.*
Giester, G., et al., "Wesselsite, SrCu[Si4O10], a further new gillespite-group mineral from the Kalahari Manganese Field, South Africa", Minerealogical Magazine, Oct. 1996, pp. 795-798, vol. 60, Mineralogical Society.
Kendrick, E., et al., "Structure and colour properties in the Egyptian Blue Family, M1-xM'xCuSi4O10, as a function of M, M' where M, M'=Ca, Sr and Ba", Dyes and Pigments, 2007, pp. 13-18, vol. 73, Elsevier Ltd.
Li, Ya-Jie, et al., "Temperature-dependent near-infrared emission of highly concentrated Cu2+ in CaCuSi4O10 phosphor", Journal of Materials Chemistry C, 2014, pp. 10395-10402, vol. 2, Royal Society of Chemistry.
Chen, Yan et al., "Hydrothermal synthesis and properties of pigments Chinese purple BaCuSi2O6 and dark blue BaCu2Si2O7", Dyes and Pigments, 2014, pp. 167-173, vol. 105, Elsevier.
Pozza, Giorgio et al., "Photoluminescence of the inorganic pigments Egyptian blue, Han blue and Han purple", Journal of Cultural Heritage, 2000, pp. 393-398, vol. 1, Elsevier.

* cited by examiner

*Primary Examiner* — C Melissa Koslow
(74) *Attorney, Agent, or Firm* — The Webb Law Firm (57) ABSTRACT

Provided is a phosphor, which is excited by a wide band of visible light, capable of emitting near-infrared light of high intensity. The phosphor comprises a crystal phase represented by a formula (1): $MCuSi_2O_6$ (where M comprises one or more of Ba, Sr and Ca), and a crystal phase represented by a formula (2): $MCuSi_4O_{10}$ (where M comprises one or more of Ba, Sr and Ca), wherein a ratio β of a diffraction peak intensity of $MCuSi_4O_{10}$ with respect to a diffraction peak intensity of $MCuSi_2O_6$ in an X-ray diffraction (XRD) pattern obtained by powder XRD measurement using CuKα rays is $0<β≤0.50$.

12 Claims, 5 Drawing Sheets

PHOSPHOR

CROSS-REFERENCE TO RELATED APPLICATIONS

This application is the United States national phase of International Application No. PCT/JP2016/053962 filed Feb. 10, 2016, and claims priority to Japanese Patent Application No. 2015-040471 filed Mar. 2, 2015, the disclosures of which are hereby incorporated in their entirety by reference.

TECHNICAL FIELD

The present invention relates to a phosphor, which is excited by visible light, capable of emitting near-infrared light.

BACKGROUND ART

In a case of evaluating objects by using a spectrometer, light in a near-infrared region is less absorbed by moisture. Therefore, a near-infrared spectrometer using a near-infrared luminescent device is particularly suitable for evaluating objects, which contain a large amount of water, such as biological objects, fruits and vegetables.

In addition, since an optical coherence tomography (OCT) uses near-infrared light, the optical coherence tomography (OCT) has characteristics that biological damage thereof is lower than that of a general X-ray tomography, and spatial resolution of tomographic images is excellent.

Further, in a solar battery or a solar power generator using silicon, photo-responsibility of silicon in a near-infrared region is the highest. Therefore, if visible light can be converted into near-infrared light, the power generation efficiency can be further enhanced.

Meanwhile, when a phosphor capable of emitting near-infrared light is used, a novel fluorescent paint or fluorescent paint printed matter can be developed. For example, conventionally, a UV light fluorescent pigment has been mainly used for forgery-proof printing utilized for paper-money or the like. If this can replace with near-infrared fluorescent pigment, novel forgery-proof printing in which the forgery, which cannot be detected with the naked eye, can be detected by a solid-state imaging device using a photo-diode made of silicon, InGaAs or the like, or equipment using a photomultiplier tube, becomes possible.

As such, it is expected that the near-infrared luminescent phosphor, which is excited by visible light, capable of emitting near-infrared light can be used for various applications in the future.

For example, Japanese Patent Application Laid-Open No. 2008-185378 discloses a near-infrared luminescent phosphor which contains $Yb_2O_3$ and $Nd_2O_3$ as an infrared glass phosphor used for OCT apparatus, further contains glass comprising $Bi_2O_3$ and $B_2O_3$, and is excited by blue light. Further, Japanese Translation of PCT International Application Publication No. 2004-526330 discloses a near-infrared luminescent body which is near-infrared light-excited by a glass-ceramic material in which transition metal ions are doped, and also proposes its expansion to OCT apparatus.

These phosphors have an advantage of having a wide fluorescence spectrum. However, when the phosphors are practically used, there has been a problem that the excited spectrum is narrow. Particularly, there has been a demand of developing a phosphor that is excited by a wide band of visible light, and has a wide fluorescence spectrum.

However, there are few kinds of near-infrared luminescent phosphor which have been conventionally known. For example, in the aforementioned Japanese Patent Application Laid-Open No. 2008-185378, the infrared glass phosphor which contains $Yb_2O_3$ and $Nd_2O_3$ as the infrared glass phosphor used for OCT apparatus, and further contains glass comprising $Bi_2O_3$ and $B_2O_3$, has been disclosed at best.

Thus, the present invention provides a novel phosphor, which is excited by visible light of a wide band, capable of emitting near-infrared light with high intensity.

SUMMARY OF THE INVENTION

The present invention proposes a phosphor comprising a crystal phase represented by a formula (1): $MCuSi_2O_6$ (where M comprises one or two or more of Ba, Sr and Ca) and a crystal phase represented by a formula (2): $MCuSi_4O_{10}$ (where M comprises one or two or more of Ba, Sr and Ca), wherein, in an X-ray diffraction (XRD) pattern obtained by powder XRD measurement using $CuK\alpha$ rays, a ratio $\beta$ of a diffraction peak intensity of $MCuSi_4O_{10}$ with respect to a diffraction peak intensity of $MCuSi_2O_6$ is $0 < \beta \leq 0.50$.

The phosphor proposed by the present invention is excited by visible light of a wide band, and can emit near-infrared light with high intensity. Therefore, as described above, the phosphor can be suitably used as a phosphor constituting a luminescent device mounted on a near-infrared spectrometer or an optical coherence tomography (OCT), and further as a wavelength conversion material constituting a light-receiving device mounted on a solar battery, a solar power generator or the like. In addition, the phosphor proposed by the present invention can be suitably used as a phosphor which is contained in fluorescent paint used for a fluorescent paint printed matter or a printed matter having an image recognition part of near-infrared light luminescence.

MODE(S) FOR CARRYING OUT THE INVENTION

Next, the present invention will be described based on embodiments for carrying out the present invention. However, the present invention is not limited to the embodiments that will be described below.

The phosphor according to an example of the present embodiment (referred to as "the present phosphor") is a phosphor containing at least a crystal phase represented by a formula (1): $MCuSi_2O_6$ (where M comprises one or two or more of Ba, Sr and Ca) (referred to as "$MCuSi_2O_6$ crystal phase") and a crystal phase represented by a formula (2): $MCuSi_4O_{10}$ (where M comprises one or two or more of Ba, Sr and Ca) (referred to as "$MCuSi_4O_{10}$ crystal phase").

By containing the $MCuSi_2O_6$ crystal phase and the $MCuSi_4O_{10}$ crystal phase, a band of an excitation spectrum can be expanded while maintaining fluorescence spectrum intensity.

The present phosphor may be a polycrystal body comprising a plurality of crystal phases, or a mixture containing a plurality of crystal phases.

Meanwhile, in a case of expressing the $MCuSi_2O_6$ crystal phase, when the "crystal phase" contains $MCuSi_2O_6$ as a main component, the "crystal phase" may also contain the other components, for example, a component present in a crystal phase, which cannot be detected by XRD. Same applies to another crystal phase.

In the present phosphor, the $MCuSi_2O_6$ crystal phase is preferably a main crystal phase. In other words, in an X-ray diffraction (XRD) pattern obtained by powder XRD measurement using CuKα rays, it is preferable that a diffraction peak intensity derived from the crystal phase of $MCuSi_2O_6$ is larger than a diffraction peak intensity derived from any other crystal phases.

Further, as for the present phosphor, in an X-ray diffraction (XRD) pattern obtained by measuring the present phosphor by powder XRD measurement using CuKα rays, a ratio β of a diffraction peak intensity of $MCuSi_4O_{10}$ with respect to a diffraction peak intensity of $MCuSi_2O_6$ is $0<\beta\leq0.50$.

When containing $MCuSi_2O_6$ and $MCuSi_4O_{10}$ in such a range, a band of an excitation spectrum can be expanded while maintaining fluorescence spectrum intensity.

From such points of view, it is preferable that a ratio β of a diffraction peak intensity of $MCuSi_4O_{10}$ with respect to a diffraction peak intensity of $MCuSi_2O_6$ is $0<\beta\leq0.50$. Among others, it is more preferably $0<\beta\leq0.31$, and furthermore preferably $0<\beta\leq0.10$.

At this time, the content of each of the crystal phases is expressed by the diffraction peak intensity of each of the crystal phases in the XRD pattern, not by chemical analysis. This is because when the content of each of the crystal phases is represented by chemical analysis, it is largely affected by a blending amount of an additive such as flux, and thus the characteristics of the present phosphor are difficult to be expressed accurately. In contrast, when the content of each of the crystal phases is expressed by the diffraction peak intensity of each of the crystal phases in the XRD pattern, the effect by the blending amount of the additive can be suppressed, and thus the characteristics of the present phosphor can be expressed accurately.

It is preferable that the present phosphor further contains a $SiO_2$ crystal phase. However, the present phosphor may not contain the $SiO_2$ crystal phase.

When the present phosphor contains the $SiO_2$ crystal phase, in an X-ray diffraction (XRD) pattern obtained by measuring the present phosphor by powder XRD measurement using CuKα rays, it is preferable that a ratio α of a diffraction peak intensity of $SiO_2$ with respect to a diffraction peak intensity of $MCuSi_2O_6$ is $0<\alpha<0.45$. When containing the $SiO_2$ crystal phase in such a range, scattering of excitation light can be prevented, and higher fluorescence spectrum intensity can be obtained.

From such points of view, it is preferable that a ratio α of a diffraction peak intensity of $SiO_2$ is $0<\alpha<0.45$, more preferably $0.16<\alpha$, and even more preferably $\alpha<0.35$. Among others, it is particularly preferably $\alpha<0.3$, and furthermore preferably $0.20<\alpha$ or $\alpha<0.25$.

Meanwhile, the present phosphor may contain, or may not contain a $BaSi_2O_5$ crystal phase. This is because, by containing the $BaSi_2O_5$ crystal phase, both an advantage and a disadvantage are not confirmed at the present time.

In addition, it is preferable that a part of Cu in the formula (1): $MCuSi_2O_6$ or the formula (2): $MCuSi_4O_{10}$, or both the formulae is substituted by Mg or Zn, or both of these. This is because even when a part of Cu is substituted by Mg or Zn, or both of these, adverse effects such as obstruction of luminescence at a local structure of $Cu(CuO_4)$ can be suppressed. Further, this is because, by forming $MgO_4$ or $ZnO_4$ in the crystal structure, self-absorption of luminescence by adjacent $CuO_4$ each other can be prevented, and thus an improvement of quantum efficiency can be expected.

It is preferable that the present phosphor further contains one or two or more elements selected from a group consisting of Li, Na, K, B, P, F, Cl, Br and I. At this time, the contents of these elements are preferably 0.005 to 3% by mass. Among others, it is more preferably 0.008% by mass or more or 2% by mass or less, and even more preferably 0.01% by mass or more or 1% by mass or less.

When the present phosphor contains these elements, luminescent peak intensity can be consequently enhanced. These elements can be added as a part of a sintering aid.

The present phosphor may contain element components other than the above when the contents of the element components other than the above are less than 20% by mass. This is because, it can be considered that the characteristics of the present phosphor are not affected by the other element components in such an amount.

The present phosphor is not limited to the forms such as a film shape, a plate shape and a particle shape. However, from a point of view of workability to a luminescent device-mounted unit or a printed matter to be used, the form of the present phosphor is preferably a particle shape.

<Production Method of the Present Phosphor>

The present phosphor can be produced by the following production method. However, the production method of the present phosphor is not limited to the production method to be described below.

The present phosphor can be obtained by mixing M element raw material in the formula (1): $MCuSi_2O_6$, Cu raw material, and silicon raw material, adding flux (sintering aid) if necessary, and calcining the mixture.

In so doing, examples of the M element raw material may include an oxide of M elements (one or two or more elements of Ba, Sr and Ca), carbonate, nitrate, acetate, and the like.

Examples of the Cu raw material may include an oxide of Cu, carbonate, sulfate, metal, and the like.

Examples of the silicon raw material may include an oxide of silicon, carbide, nitride, silicon, and the like.

Incidentally, from a point of view of keeping a divalent oxidation number of Cu, it is preferable that a reducing agent is not added.

A blending ratio (molar ratio) of the M element raw material and the Cu raw material is preferably 1.5:1.0 to 0.8:1.0. Among others, it is more preferably 1.3:1.0 to 0.9:1.0, and even more preferably 1.2:1.0 to 1.0:1.0. In addition, a blending ratio (mass ratio) of the Cu raw material and the silicon raw material is preferably 1.0:2.0 to 1.0:5.0. Among others, it is more preferably 1.0:3.0 to 1.0:4.5, and even more preferably 1.0:3.5 to 1.0:4.2.

By blending flux (sintering aid), a chemical reaction can be promoted, and thus unreacted substances can be reduced.

Examples of the flux (sintering aid) may include a flux (sintering aid) containing one or two or more elements selected from a group consisting of Li, Na, K, B, P, F, Cl, Br and I. Among others, it is more preferably Li, Na, K, B, F, Cl, and the like.

A blending amount (mass ratio) of the flux (sintering aid) is preferably 0.1 to 15% with respect to a total weight obtained by mixing the M element raw material, the Cu raw material and the silicon raw material. Among others, it is more preferably 1% or more or 10% or less, and even more preferably 2% or more or 7% or less.

As for a calcination atmosphere, if it is not a reducing atmosphere, any atmosphere can be appropriately employed. For example, an inert gas atmosphere, an air atmosphere, an acidic atmosphere and the like can be employed.

A calcination temperature may be 700 to 1,100° C. This is because when it is less than 700° C., a reaction is hardly progressed. In contrast, when it is 1,100° C. or more, there is a possibility of melting.

In addition, the calcination may be repeated several times. That is, for example, the first calcination is performed in a temperature range of 700 to 900° C., the calcined powder thus obtained is crushed, and then the second calcination can be also performed in a temperature range of 800 to 1,100° C.

Further, the calcined powder is washed with an acidic solution such as water and hydrochloric acid after the first calcination, and then the second calcination can be also performed. By doing so, the blending amount of the sintering aid can be more appropriately adjusted to each calcination step, and thus the element contents of Li, Na, K, B, P, F, Cl, Br and I contained in the present phosphor which is a final product can be also easily controlled in an appropriate range.

<Characteristics of the Present Phosphor>

The present phosphor is excited by visible light, and can emit near-infrared light. That is, the present phosphor has characteristics of having an excitation spectrum in a visible light region (380 nm to 750 nm), and having a luminescent peak in a near-infrared region (750 nm to 2,500 nm).

In addition, as one of the characteristics of the present phosphor, a point that an excitation band is wide can be cited. For example, an excitation band width of 80% or more of the maximum excitation intensity can be set to 90 nm or more, more preferably 100 nm or more, and even more preferably 150 nm or more.

Further, by containing a crystal phase represented by $MCuSi_4O_{10}$, or a crystal phase such as cristobalite, tridymite and quartz, which is represented by $SiO_2$, the present phosphor has a characteristic that a luminescent intensity in a near-infrared region can be further enhanced.

<Applications>

For example, the present phosphor is mixed with an organic resin or an inorganic filler, for example, glass particles, a metal oxide or the like, and further a solvent, a dispersant or the like if necessary, coated and formed as a liquid composition, and then solidified via drying or/and curing. Thus, the present phosphor can be used as a form of a phosphor composition layer, a phosphor composition filler or the like.

Since the present phosphor is excited by visible light, and can emit near-infrared light, the present phosphor can be used for a near-infrared luminescent device. By using the near-infrared luminescent device, the present phosphor can be suitably used as a phosphor constituting a luminescent device mounted on luminescent device mounted units such as a near-infrared spectrometer and an optical coherence tomography (OCT), as a wavelength conversion material constituting a light-receiving device mounted on light-receiving device mounted units such as a solar power generator, and as a phosphor which is contained in fluorescent paint used for a fluorescent paint printed matter or a printed matter having an image recognition part of near-infrared light luminescence.

When the near-infrared luminescent device containing the present phosphor (referred to as "the present near-infrared luminescent device") is used for a spectrometer, the spectrometer can be used for an evaluation apparatus of biological objects, fruits and vegetables, or the like.

In the spectrometer, the present phosphor is mounted as a wavelength conversion material of a near-infrared light source.

In addition, when the light-receiving device containing the present phosphor is used for a solar power generator, a visible light component of sunlight can be converted into near-infrared light, and thus the power generation efficiency can be further enhanced.

In a solar power generator, the present phosphor can be mounted as a wavelength conversion material on a light-receiving side. Particularly, it is known that a light-receiving device using a silicon photo-diode has high spectral sensitivity in a wavelength band of near-infrared light of 800 to 1,000 nm, and thus the present phosphor is suitable as a wavelength conversion material having an excellent matching property with 900 to 950 nm, which is a peak wavelength band of near-infrared luminescence of the present phosphor.

Meanwhile, since the present phosphor emits near-infrared light even when electron rays, X-rays or the like are used as an excitation source, for example, when using X-rays as an excitation source, applications into an X-ray diagnostic apparatus for medical or security as a scintillation material, or the like are possible.

Further, when a fluorescent paint is produced by using the present phosphor, for example, a fluorescent paint printed matter which is used for forgery-proof printing utilized for paper-money or the like can be produced, and then novel forgery-proof printing in which the forgery, which cannot be detected with the naked eye, can be detected by a solid-state imaging device using a photo-diode made of silicon, InGaAs or the like, or equipment using a photomultiplier tube, can be performed.

These fluorescent paints are mixed with a fluidity adjusting material of inorganic components or organic components, an organic solvent, or the like, as setting transparent resin components as matrix in addition to the present phosphor, and prepared as ink or paste. Examples of the resin component may include an epoxy resin, a phenol resin, a silicone resin, an acrylic resin, and polymethyl methacrylate. Additionally, glass particles, which are light scattering components, may be mixed if necessary.

<Description of Terms>

In the present invention, when the term "X to Y" (X and Y are arbitrary numbers) is expressed, unless particularly stated otherwise, the expression includes the meaning of "X or more and Y or less", as well as the meaning of "preferably more than X" or "preferably less than Y".

Further, when the term "X or more" (X is an arbitrary number) or "Y or less" (Y is an arbitrary number) is expressed, the expression includes the meaning of "more than X is preferable" or "less than Y is preferable".

EXAMPLES

Hereafter, the present invention will be described in further detail based on the examples and comparative examples described below.

<XRD Measurement>

Each of the phosphors (samples) obtained in Examples and Comparative Examples served as a sample for powder X-ray diffraction measurement (XRD). The sample was mounted on a holder, and angles and intensities of the diffracted rays were measured using MXP18 (manufactured by Bruker AXS) under the following conditions, thereby obtaining an XRD pattern.

(Tube) Cu Kα ray
(Tube voltage) 40 kV
(Tube current) 150 mA
(Sampling interval) 0.02°
(Scanning speed) 4.0°/min
(Initiation angle) 5.02°
(Termination angle) 80°

<Measurement of Fluorescence Characteristics>

Each of the phosphors (samples) obtained in Examples and Comparative Examples served as a sample for luminescent characteristic measurement, and an excitation spectrum and a fluorescence spectrum were measured using a spectrofluorometer (FP-8600, manufactured by JASCO Corp.) under conditions in which the band widths of both the excitation side and the fluorescence side were 10 nm and the scanning speed was 1,000 nm/min.

The excitation spectrum was evaluated by the following criteria.

A: an excitation band width of 80% or more of the maximum excitation intensity is 120 nm or more.

B: an excitation band width of 80% or more of the maximum excitation intensity is 90 nm or more.

C: an excitation band width of 80% or more of the maximum excitation intensity is less than 90 nm.

Each of the fluorescence spectra in excitation wavelengths (620 nm, 570 nm and 520 nm) was evaluated by the following criteria.

A: a peak intensity is 4,000 counts or more.

B: a peak intensity is 3,000 counts or more and less than 4,000 counts.

C: a peak intensity is less than 3,000 counts.

(Overall Evaluation)

The four evaluation items, that is, the excitation band width of the evaluated excitation spectrum and the peak intensity of the fluorescence spectrum in each of the excitation wavelengths (620 nm, 570 nm and 520 nm), were evaluated by the following criteria.

AA: the four evaluation items are all A.

A: the four evaluation items are A or B, and the number of A is 2 or more.

B: the four evaluation items are A or B, and the number of A is 1 or less.

C: the number of C in the four evaluation items is 1 or more.

Example 1

$BaCO_3$, CuO and $SiO_2$ were mixed such that a molar ratio of those was 1:1:3.5. Further, $BaCl_2$ as flux was added to the mixture such that the total amount of the mixture became 3% by mass, and was mixed. The mixture was put in an alumina crucible, and was calcined at 1,000° C. for 24 hours under the air, thereby obtaining a phosphor (sample).

Figure 1:
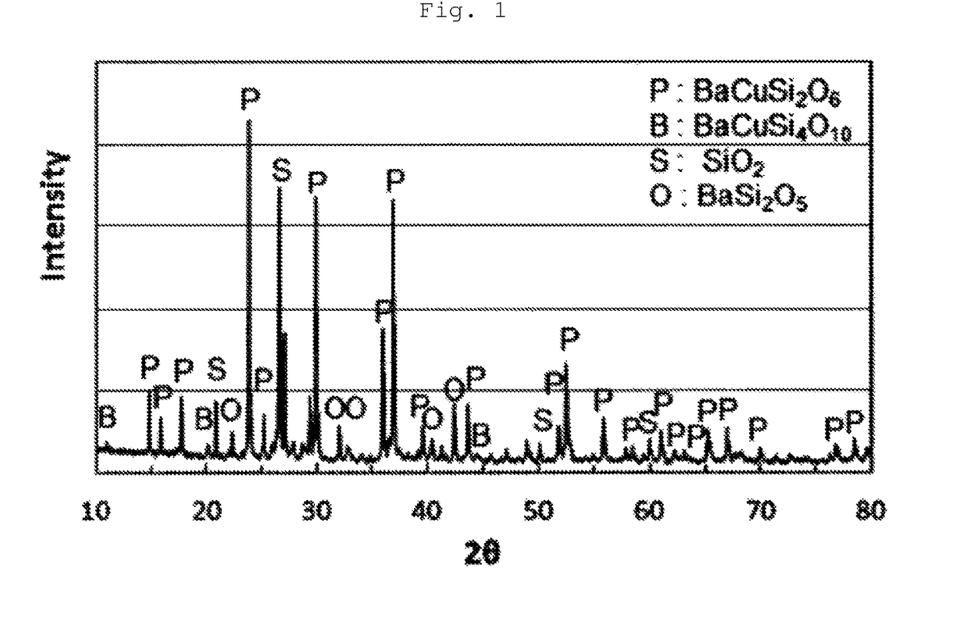
FIG. 1 is a drawing which illustrates an XRD pattern of the phosphor (sample) obtained in Example 1.

An XRD pattern of the obtained phosphor (sample) is illustrated in FIG. 1.

The obtained phosphor (sample) was a compound composed of a $BaCuSi_2O_6$ phase as a main crystal phase, and containing a $SiO_2$ phase, a trace amount of $BaCuSi_4O_{10}$ phase, and a $BaSi_2O_5$ phase.

A Cl amount contained in the compound was 0.02% by mass by the fluorescence X-ray measurement.

Example 2

$BaCO_3$, CuO and $SiO_2$ were mixed such that a molar ratio of those was 1:1:4. Further, $BaCl_2$ as flux was added to the mixture such that the total amount of the mixture became 3% by mass, and was mixed. The mixture was put in an alumina crucible, and was calcined at 1,000° C. for 24 hours under the air, thereby obtaining a phosphor (sample).

Figure 2:
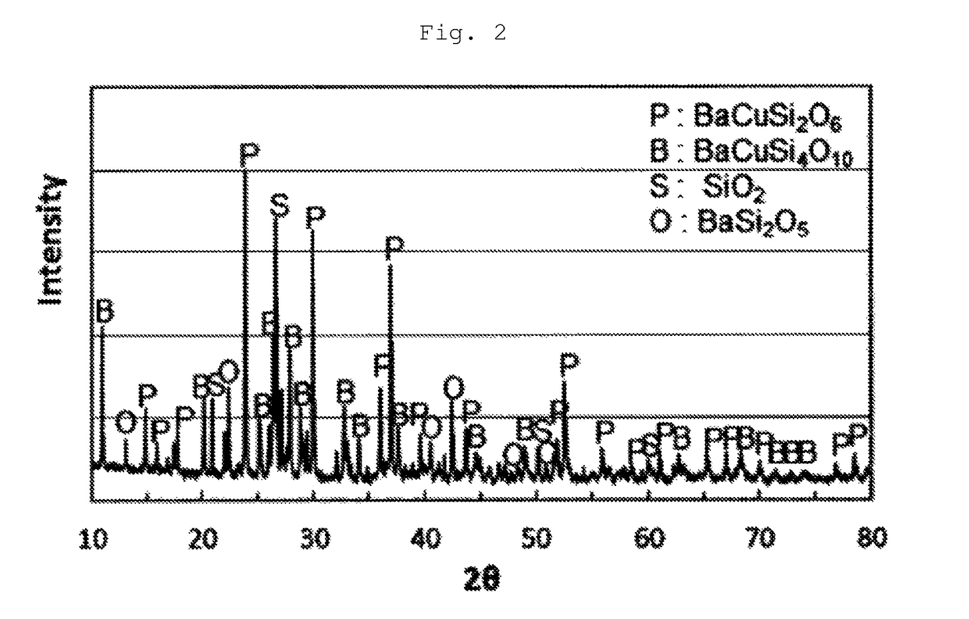
FIG. 2 is a drawing which illustrates an XRD pattern of the phosphor (sample) obtained in Example 2.

An XRD pattern of the obtained phosphor (sample) is illustrated in FIG. 2.

The obtained phosphor (sample) was a compound composed of a $BaCuSi_2O_6$ phase as a main crystal phase, and containing a $SiO_2$ phase, a $BaCuSi_4O_{10}$ phase, and a $BaSi_2O_5$ phase.

A Cl amount contained in the compound was 0.01% by mass by the fluorescence X-ray measurement.

Comparative Example 1

$BaCO_3$, CuO and $SiO_2$ were weighed such that a molar ratio of those was 1:1:4, and were wet mixed in acetone.

The mixture was put in an alumina crucible, and was calcined at 960° C. for 16 hours under the air, thereby obtaining a phosphor (sample).

Figure 3:
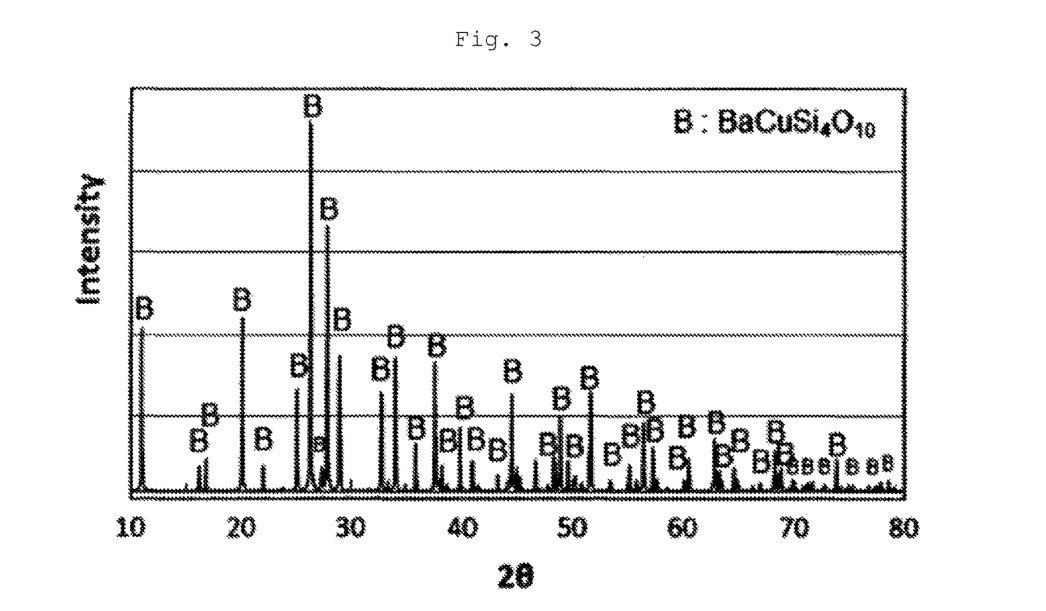
FIG. 3 is a drawing which illustrates an XRD pattern of the phosphor (sample) obtained in Comparative Example 1.

An XRD pattern of the obtained phosphor (sample) is illustrated in FIG. 3.

The obtained phosphor (sample) was a single phase of $BaCuSi_4O_{10}$.

Each of the contents of halogen elements such as Cl, alkaline metals such as Na, and P in the phosphor (sample) was less than 0.005% by mass by the fluorescence X-ray measurement.

Comparative Example 2

$BaCO_3$, CuO and $SiO_2$ were mixed such that a molar ratio of those was 1:1:2. Then, the mixture was put in an alumina crucible, and was calcined at 1,000° C. for 24 hours under the air, thereby obtaining a phosphor (sample).

Figure 4:
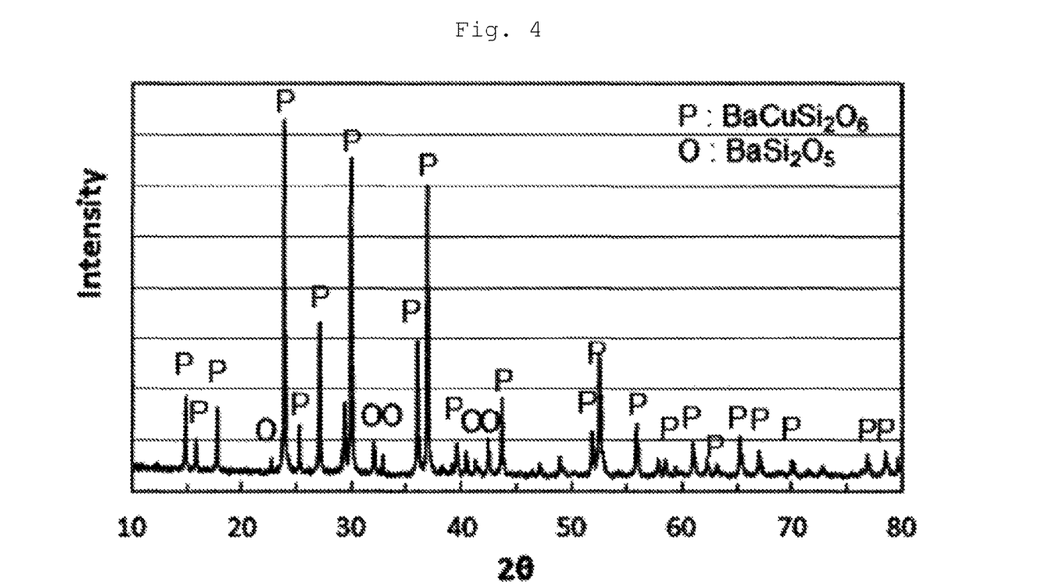
FIG. 4 is a drawing which illustrates an XRD pattern of the phosphor (sample) obtained in Comparative Example 2.

An XRD pattern of the obtained phosphor (sample) is illustrated in FIG. 4.

The obtained phosphor (sample) was a compound composed of a $BaCuSi_2O_6$ phase as a main crystal phase, and containing a trace amount of $BaSi_2O_5$ phase.

Each of the contents of halogen elements such as Cl, alkaline metals such as Na, and P, which were contained in the compound, was less than 0.005% by mass by the fluorescence X-ray measurement.

Comparative Example 3

$BaCO_3$, CuO and $SiO_2$ were mixed such that a molar ratio of those was 1:1:3. Then, the mixture was put in an alumina crucible, and was calcined at 1,000° C. for 24 hours under the air, thereby obtaining a phosphor (sample).

Figure 5:
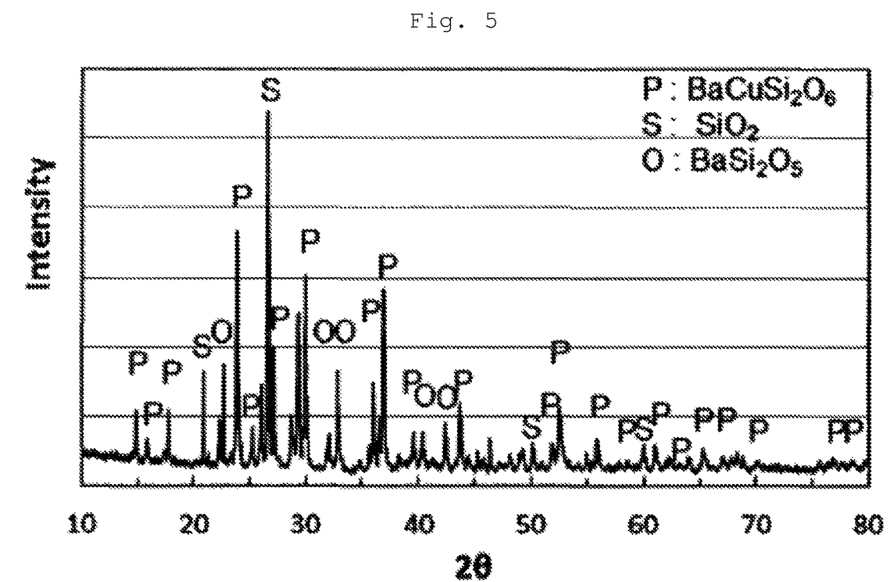
FIG. 5 is a drawing which illustrates an XRD pattern of the phosphor (sample) obtained in Comparative Example 3.

An XRD pattern of the obtained phosphor (sample) is illustrated in FIG. 5.

The obtained phosphor (sample) was a compound composed of a $SiO_2$ phase as a main crystal phase, and containing a $BaCuSi_2O_6$ phase and a trace amount of $BaSi_2O_5$ phase.

Each of the contents of halogen elements such as Cl, alkaline metals such as Na, and P, which were contained in the compound, was less than 0.005% by mass by the fluorescence X-ray measurement.

Comparative Example 4

$BaCO_3$, $Cu_2CO_3.(OH)_2.H_2O$ and $SiO_2$ were mixed such that a molar ratio of those was 1:0.5:4, and were wet mixed in ethanol. The mixture was put in an alumina crucible, and was calcined at 1,100° C. for 24 hours under the air, thereby obtaining a phosphor (sample).

Figure 6:
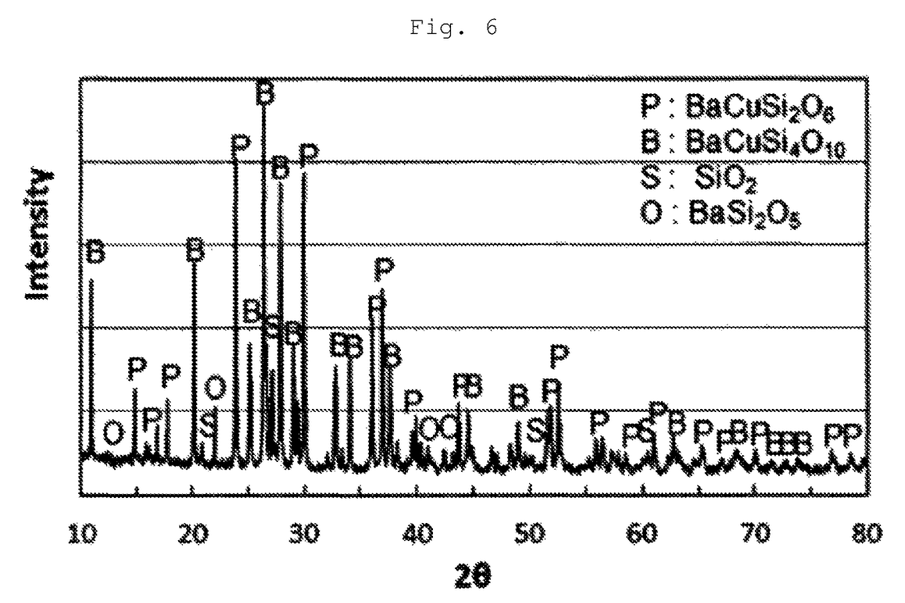
FIG. 6 is a drawing which illustrates an XRD pattern of the phosphor (sample) obtained in Comparative Example 4.

An XRD pattern of the obtained phosphor (sample) is illustrated in FIG. 6.

The obtained phosphor (sample) was a compound composed of a $BaCuSi_4O_{10}$ phase and a $BaCuSi_2O_6$ phase as a main crystal phase, and containing a $SiO_2$ phase and a $BaSi_2O_5$ phase.

Figure 7:
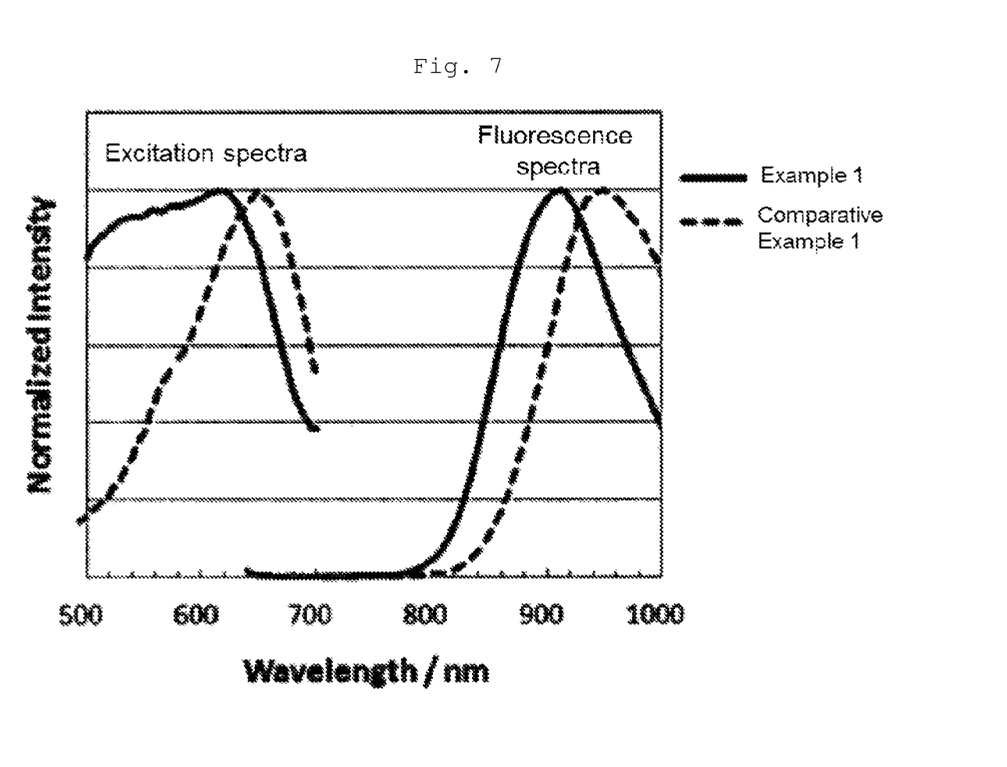
FIG. 7 is a drawing which illustrates excitation spectra and fluorescence spectra of Example 1 and Comparative Example 1 as relative values when the maximum values of excitation intensity and fluorescence intensity in the vertical axis are normalized as 1.

Each of the contents of halogen elements such as Cl, alkaline metals such as Na, and P, which were contained in the compound, was less than 0.005% by mass by the fluorescence X-ray measurement.

or a plurality of single-color light sources is used, conversion efficiency to near-infrared light can be further enhanced.

Meanwhile, in Comparative Example 1, dependency of an excitation wavelength is large, and an excitation wavelength band in which a fluorescent intensity difference can be suppressed within 20%, is limited to a narrow range of 615 to 680 nm. That is, a usable excitation light source is limited to a red light source, and the conversion efficiency to near-infrared light is suppressed low.

Next, an effect of comprising the $BaCuSi_4O_{10}$ phase was studied.

Figure 8:
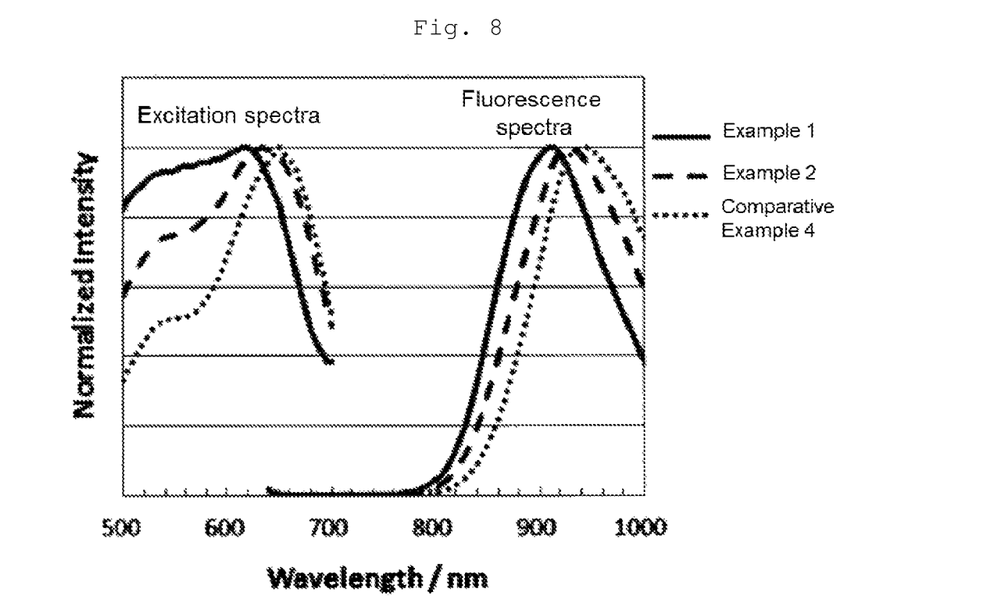
FIG. 8 is a drawing which illustrates excitation spectra and fluorescence spectra of Example 1, Example 2 and Comparative Example 4 as relative values when the maximum values of excitation intensity and fluorescence intensity in the vertical axis are normalized as 1.

FIG. 8 is a drawing which illustrates excitation spectra and fluorescence spectra of Example 1, Example 2 and Comparative Example 4 when the maximum values of excitation intensity and fluorescence intensity in the vertical axis are normalized as 1.

When collating with the XRD patterns of each of Examples, it was found that wavelength dependency of the fluorescence spectrum was enlarged along with an increase of the $BaCuSi_4O_{10}$ phase. This is consistent even when considering the result of the $BaCuSi_4O_{10}$ single phase in Comparative Example 1.

Figure 9:
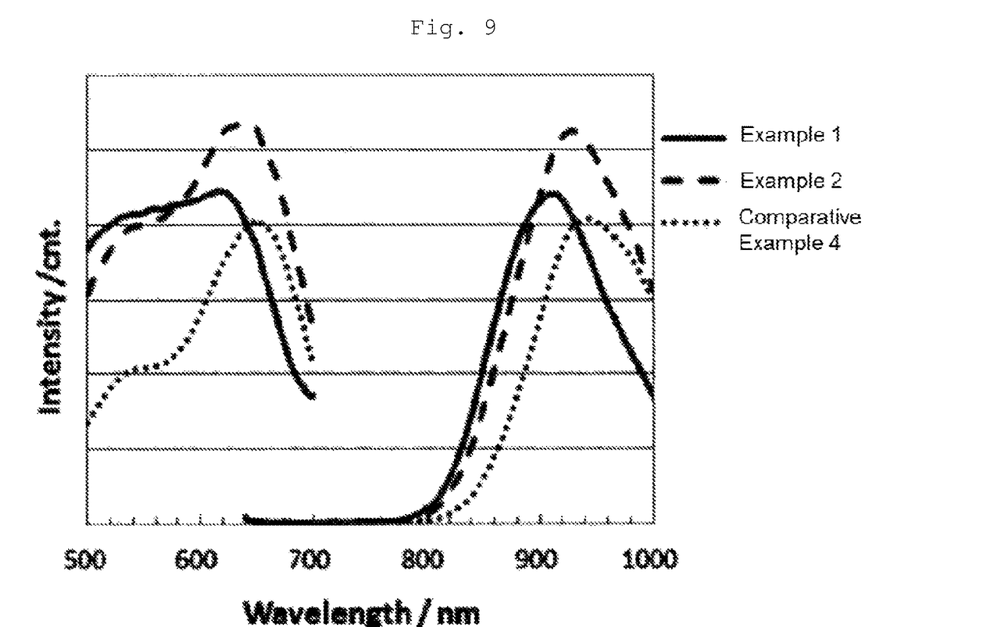
FIG. 9 is a drawing which compares excitation spectrum intensities to fluorescence spectrum intensities of Example 1, Example 2 and Comparative Example 4.

FIG. 9 is a drawing which compares excitation spectrum intensities to fluorescence spectrum intensities of Example 1, Example 2 and Comparative Example 4.

It is found that the spectrum intensities are from low to high in the order of Comparative Example 4<Example 1<Example 2. By comprising the $BaCuSi_4O_{10}$ phase inten-

TABLE 1

| | Crystal phase | | | Peak intensity ratio α $SiO_2$/$BaCuSi_2O_6$ | Peak intensity ratio β $BaCuSi_4O_{10}$/$BaCuSi_2O_6$ | Fluorescence characteristics | | | | | | | |
|---|---|---|---|---|---|---|---|---|---|---|---|---|---|
| | | | | | | Excitation | | Fluorescence spectra | | | | | |
| | 1 1 2 6 phase $BaCuSi_2O_6$ | 1 1 4 10 phase $BaCuSi_4O_{10}$ | 0 0 1 2 phase $SiO_2$ | | | spectra Excitation band width (nm) | | Peak wave-length (nm) | Peak intensity 620 nm excitation | | Peak intensity 570 nm excitation | | Peak intensity 520 nm excitation | Over-all evalu-ation |
| Example 1 | Con-tained | Con-tained | Con-tained | 0.21 | 0.08 | 152 | A | 913 | 4440 | A | 4237 | A | 4000 A | AA |
| Example 2 | Con-tained | Con-tained | Con-tained | 0.31 | 0.31 | 94 | B | 928 | 5217 | A | 4137 | A | 3660 B | A |
| Comparative Example 1 | None | Con-tained | None | — | — | 67 | C | 948 | — | | — | | — | C |
| Comparative Example 2 | Con-tained | None | None | 0 | 0 | >156 | A | 906 | 1553 | C | 1642 | C | 1526 C | C |
| Comparative Example 3 | Con-tained | None | Con-tained | 0.45 | 0 | >150 | A | 913 | 1345 | C | 1507 | C | 1446 C | C |
| Comparative Example 4 | Con-tained | Con-tained | Con-tained | 0.16 | 0.69 | 60 | C | 942 | 3483 | B | 2164 | C | 1810 C | C |

(Considerations)

FIG. 7 is a drawing which illustrates excitation spectra and fluorescence spectra of Example 1 and Comparative Example 1 as relative values when the maximum values of excitation intensity and fluorescence intensity in the vertical axis are normalized as 1.

When focusing on the excitation spectra, Example 1 shows that wavelength dependency is small, and an intensity difference in a range of 500 nm to 650 nm falls within 20% or less. That is, if the excitation is made within a wavelength of this range, it is found that a fluorescent intensity difference can be suppressed within 20%, and the wavelength dependency is small. This shows that if a white light source tionally while comprising the $BaCuSi_2O_6$ phase as a main crystal phase in the same manner as Example 2, it was found that excitation efficiency in a range of 580 to 700 nm was increased, and along with this, fluorescent intensity could be improved. However, when the amount of the $BaCuSi_4O_{10}$ phase is too large, it is also confirmed that the wavelength dependency of the excitation band tends to be strong.

From the results of Examples as described above and the results of the various tests carried out by the inventors so far, when a ratio of the $BaCuSi_2O_6$ phase is increased, a band of the excitation spectrum is expanded. On the other hand, there is a tendency that the luminescent intensity is decreased. Thus, from a point of view of expanding the band of the excitation spectrum while maintaining the luminescent intensity, it is preferable to comprise an appropriate amount of the BaCuSi$_4$O$_{10}$ phase while comprising the BaCuSi$_2$O$_6$ phase as a main crystal phase. In other words, when a ratio of an intensity I$_B$ of a BaCuSi$_4$O$_{10}$ diffraction ray peak located in 2θ of 19.5 to 20.5° and an intensity I$_P$ of a BaCuSi$_2$O$_6$ diffraction ray peak located in 2θ of 23.5 to 24.5° is designated as an intensity ratio β (=I$_B$/I$_P$), it can be considered that a preferable range thereof is 0<β≤0.50, among them, more preferably 0<β≤0.31, and even more preferably 0<β≤0.10. In Example 1, it was β=0.08.

Next, an effect of comprising the SiO$_2$ phase was studied.

The excitation spectrum intensities and the fluorescence spectrum intensities of Example 1, Comparative Example 2 and 3 were compared (see Table 1).

The spectrum intensities were from low to high in the order of Comparative Example 2≈Comparative Example 3<Example 1. In contrast, the contents of the SiO$_2$ phase were from low to high in the order of Comparative Example 2<Example 1<Comparative Example 3.

From the results of Examples as described above and the results of the various tests carried out by the inventors so far, there is no practical problem even when the SiO$_2$ phase is not contained. On the other hand, in the case of containing the SiO$_2$ phase, when a ratio of an intensity Is of a SiO$_2$ diffraction ray peak located in 2θ of 20.6° to 21.1° and an intensity I$_P$ of a BaCuSi$_2$O$_6$ diffraction ray peak located in 2θ of 23.5 to 24.5° is designated as an intensity ratio α (=I$_S$/I$_P$), it can be considered that a preferable range thereof is 0<α<0.45, and among them, more preferably 0.1<α or α<0.3. In Example 1, it was α=0.21.

Incidentally, since a SiO$_2$ main peak (near 2θ of 26.6°) is overlapped with a peak of BaCuSi$_2$O$_6$ (near 2θ of 27.1°), it was judged that the SiO$_2$ main peak (near 2θ of 26.6°) was inappropriate to be used for the calculation of the intensity ratio.

Since alkaline earth metals such as Ba, Sr and Ca have similar properties, even when using Sr or Ca instead of Ba, or with Ba, it can be considered that the same effect as the above Examples can be obtained.

The invention claimed is:

1. A phosphor, comprising
a crystal phase represented by a formula (1): MCuSi$_2$O$_6$ (where M comprises one or two or more of Ba, Sr and Ca) and
a crystal phase represented by a formula (2): MCuSi$_4$O$_{10}$ (where M comprises one or two or more of Ba, Sr and Ca),
wherein, in an X-ray diffraction (XRD) pattern obtained by powder XRD measurement using CuKα rays, a ratio β of a diffraction peak intensity of MCuSi$_4$O$_{10}$ with respect to a diffraction peak intensity of MCuSi$_2$O$_6$ is 0<β≤0.50,
wherein the phosphor further comprises a SiO$_2$ crystal phase, and
wherein, in an X-ray diffraction (XRD) pattern obtained by powder XRD measurement using CuKα rays, a ratio α of a diffraction peak intensity of SiO$_2$ with respect to a diffraction peak intensity of MCuSi$_2$O$_6$ is 0<α<0.45.

2. The phosphor according to claim 1, comprising a compound in which a part of Cu in the formula (1): MCuSi$_2$O$_6$ or the formula (2): MCuSi$_4$O$_{10}$, or both the formulae is substituted by Mg or Zn, or both of these.

3. The phosphor according to claim 2, further comprising one or two or more elements selected from a group consisting of Li, Na, K, B, P, F, Cl, Br and I at 0.005 to 3% by mass.

4. The phosphor according to claim 1, further comprising one or two or more elements selected from a group consisting of Li, Na, K, B, P, F, Cl, Br and I at 0.005 to 3% by mass.

5. A near-infrared luminescent device comprising the phosphor according to claim 1.

6. A unit comprising the near-infrared luminescent device according to claim 5, wherein the unit is a near-infrared spectrometer or an optical coherence tomography unit.

7. A fluorescent paint comprising the phosphor according to claim 1.

8. A substrate printed with the fluorescent paint according to claim 7.

9. A near-infrared luminescent device comprising a phosphor, wherein the phosphor comprises a crystal phase represented by a formula (1): MCuSi$_2$O$_6$ (where M comprises one or two or more of Ba, Sr and Ca) and
a crystal phase represented by a formula (2): MCuSi$_4$O$_{10}$ (where M comprises one or two or more of Ba, Sr and Ca), and
wherein, in an X-ray diffraction (XRD) pattern obtained by powder XRD measurement using CuKα rays, a ratio β of a diffraction peak intensity of MCuSi$_4$O$_{10}$ with respect to a diffraction peak intensity of MCuSi$_2$O$_6$ is 0<β≤0.50.

10. A unit comprising the near-infrared luminescent device according to claim 9, wherein the unit is a near-infrared spectrometer or an optical coherence tomography unit.

11. A fluorescent paint comprising a phosphor, wherein the phosphor comprises a crystal phase represented by a formula (1): MCuSi$_2$O$_6$ (where M comprises one or two or more of Ba, Sr and Ca) and
a crystal phase represented by a formula (2): MCuSi$_4$O$_{10}$ (where M comprises one or two or more of Ba, Sr and Ca), and
wherein, in an X-ray diffraction (XRD) pattern obtained by powder XRD measurement using CuKα rays, a ratio β of a diffraction peak intensity of MCuSi$_4$O$_{10}$ with respect to a diffraction peak intensity of MCuSi$_2$O$_6$ is 0<β≤0.50.

12. A substrate printed with the fluorescent paint according to claim 11.

* * * * *

UNITED STATES PATENT AND TRADEMARK OFFICE
CERTIFICATE OF CORRECTION

PATENT NO. : 10,538,679 B2  
APPLICATION NO. : 15/533057  
DATED : January 21, 2020  
INVENTOR(S) : Jun-ichi Itoh et al.

Page 1 of 1

It is certified that error appears in the above-identified patent and that said Letters Patent is hereby corrected as shown below:

On the Title Page

Column 2, OTHER PUBLICATIONS, Line 1, delete "2018." and insert -- 2008. --

Column 2, OTHER PUBLICATIONS, Line 7, delete "propeties" and insert -- properties --

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*